April 18, 1950 G. OHLHUS Plant Pat. 936
ROSE PLANT
Filed Jan. 10, 1949
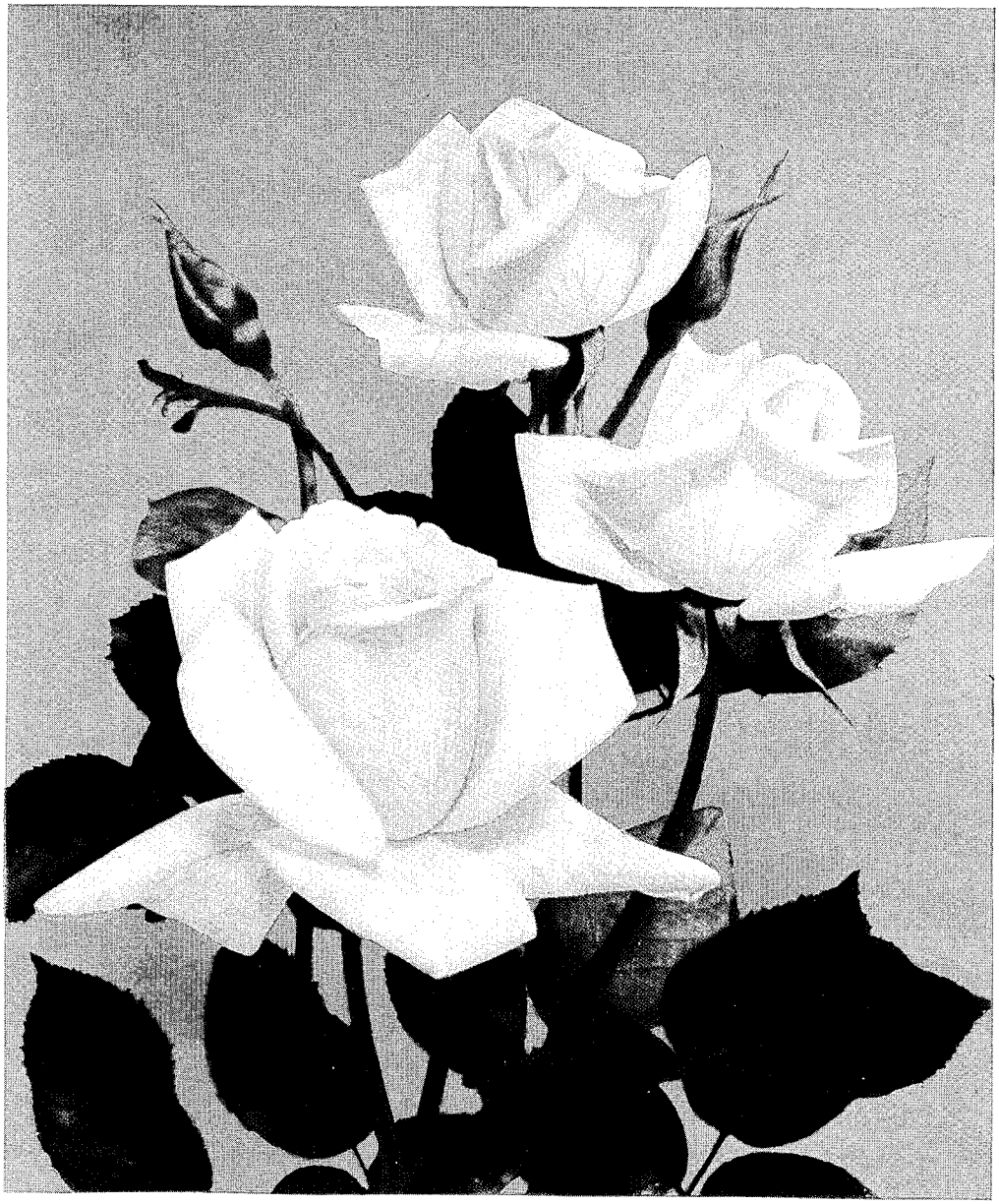
Inventor
George Ohlhus
By Robb & Robb
Attorneys Patented Apr. 18, 1950

Plant Pat. 936

UNITED STATES PATENT OFFICE

936

ROSE PLANT

George Ohlhus, West Grove, Pa., assignor to The Conard-Pyle Company, West Grove, Pa., a corporation of Pennsylvania Application January 10, 1949, Serial No. 70,123

1 Claim. (Cl. 47—61)

The present invention relates to a new and distinct variety of rose plant, distinguished from its parents and other rose varieties by the combination of its dominant characteristics, to wit, the vigorous growth habit of the plant, with the excellence of form of its bloom, including the curl of the petals and the color of the bloom that has not heretofore existed, to my knowledge.

Asexual reproduction of this new variety shows the foregoing characteristics come true to form and are established.

In the accompanying drawing are illustrated specimens of the blooms, at different stages of development from closed bud to full-open flowers, depicting as nearly as possible the unique coloring of said flowers, their perfection of form and peculiar curl of the petals.

The following is a detailed description of the new variety, all reference to color being in accordance with Ridgway's Color Standards and Nomenclature:

Type: Hardy; bush; seedling; for cut flowers and garden decoration.

Class: Hybrid tea.

Breeding: Seedling.

*Seed parent.*—"Luna" (unpatented).

*Pollen parent.*—"Mrs. Pierre S. du Pont"× "Mrs. Sam McGredy" (both unpatented).

Propagation: Holds its distinguishing characteristics through succeeding propagations by budding.

*Flower*

Locality where grown: West Grove, Pennsylvania.

Flowers borne: Singly or occasionally two or three to stem; on normal, medium length stems.

Quantity of bloom: Abundant.

Continuity: Continuous.

Fragrance: Penetrating.

Bud:

*Peduncle.*—Medium length; medium heavy; erect; medium rough; yellow prickles. Color—Lettuce Green, Plate V.

*Before calyx breaks.* — Size — medium. Form—pointed; with foliaceous appendages on the surface of the bud; with slender, slightly cut foliaceous parts extending beyond the tip of the bud equal to one-fourth or more of its length.

*As calyx breaks.*—Color—Light Green Yellow, Plate V, tinged with Flesh Color, Plate XIV.

*As first petal opens.*—Size—medium large. Form — long pointed. Color — outside: shading from Pinard Yellow, Plate IV, at base to Grenadine Pink, Plate II, near outer edges; occasionally with center band of Pale Yellow-Orange, Plate III, along midrib; inside: shading from Lemon Chrome Plate IV, at base to Capucine Orange, Plate III, over most of petal surface; occasionally with a band of Salmon Buff, Plate XIV, along midrib.

*Opening.*—Opens up well.

Bloom: Size, when fully open—large; 4 inches to 5 inches.

*Petalage.*—Double; from 25 to 30 petals arranged regularly.

*Form.*—Very high center at first; becoming high centered; petals remaining at first loosely rolled outward; becoming later, at maturity, loosely rolled outward.

Petals: Moderately thick; with inside and outside satiny.

*Shape.*—Outside—obovate. Intermediate—obovate. Inside—obovate.

*Color.*—Colors may be modified by being shaded or washed with other colors.

This description of a newly opened flower was made from a rose grown outdoors in the month of August at West Grove, Pennsylvania:

*Color.* — *Outside petal* — outside surface: shading from Pinard Yellow, Plate IV, at base to Pale Yellow-Orange, Plate III, near outer edges; occasionally with a whitish band along midrib; inside surface: Picric Yellow, Plate IV, at base, shading to Seashell Pink, Plate XIV, and Shell Pink, Plate XXVIII, at outer edge. *Intermediate petal*—outside surface: shading from Pinard Yellow, Plate IV, at base to Capucine Buff, Plate III, over most of petal surface; inside surface: shading from Pale Greenish Yellow, Plate V, at base to Warm Buff, Plate XV, over most of petal surface. *Inner petal.*—outside surface: Pale Greenish Yellow, Plate V, at base, occasionally extending down midrib, shading to Salmon Buff, Plate XIV, over most of petal surface; inside surface: shading from Pale Lemon Yellow, Plate IV, at base to Capucine Buff, Plate III, over most of petal surface.

This description was made from a rose that was open for three days outdoors in the month of August at West Grove, Pennsylvania:

*Color.* — *Outside petal* — outside surface: shading from Sulphur Yellow, Plate V, at base to Pale Ochraceous Buff, Plate XV, over most of petal surface; inside surface: shading from Pale Greenish Yellow, Plate V, at base to Buff Yellow, Plate IV, and to Seashell Pink, Plate XIV, over most of petal surface. *Inside petal*—outside surface: shading from Sulphur Yellow, Plate V, at base to Shell Pink, Plate XXVIII, or sometimes to La France Pink, Plate I, over most of petal surface; inside surface: shading from Sulphur Yellow, Plate V, at base to Shell Pink, Plate XXVIII, or sometimes to Pale Flesh Color, Plate XIV, over most of petal surface.

*General color effect.*—Newly opened flower—Salmon Buff, Plate XIV, to Seashell Pink, Plate XIV. Three days open—Pale Salmon Color, Plate XIV, to Pale Flesh Color, Plate XIV.

*Behavior.*—Drop off cleanly.

*Flower longevity.*—Cut roses grown outdoors kept at living-room temperatures, 4 to 5 days in August.

*Reproductive organs*

Stamens: Medium number; arranged regularly about pistils.

Filaments: Medium long; most with anthers. Color—Citron Yellow, Plate XVI, to Carrot Red, Plate XIV.

Anthers: Large; most open at once. Color—Cadmium Orange, Plate III.

Pollen: Moderately abundant. Color—Capucine Yellow, Plate III.

Pistils: Medium number.

Styles: Uneven; medium length; bunched.

Stigma: Colonial Buff, Plate XXX.

Ovaries: All enclosed in calyx.

Hips: Globular; rough; walls thick. Color—Parrot Green, Plate VI, with patches of russet.

Sepals: Permanent; medium length; spear-shaped.

Seeds: Many; medium large.

*Plant*

Foliage:

*Leaves.*—Compound of three to five leaflets; abundant; medium size; leathery.

*Leaflets.*—Shape—ovoid with apex acute; base round; margin simply serrate.

*Color.*—*Mature*—upper surface: Yew Green, Plate XXXI; under surface: Asphodel Green, Plate XLI. *Young*—upper surface: Oil Green, Plate V, bordered with Prussian Red, Plate XXVII; under surface: Citron Drab, Plate XL.

*Rachis.*—Medium heavy. Upper side: prickly; under side: moderately thorny.

*Stipules.*—Medium length; medium width; with medium length points turning out at an angle of more than 45° and less than 90°, recurved toward the stem.

*Disease.*—Resistant to mildew and blackspot.

Growth:

*Habit.*—Upright; branched.

*Growth.*—Vigorous.

*Canes.*—Heavy.

*Main stems.*—Gray-green. *Thorns*—Several; medium length; hooked downward; with medium length narrow base. *Prickles and hairs*—None.

*Branches.*—Reddish green. *Thorns*—Several; medium length; hooked downward; with short narrow base. *Prickles and hairs*—none.

*New shoots.*—*Color*—Lettuce Green, Plate V. *Thorns*—many; medium length; hooked downward; with short narrow base. *Prickles and hairs*—none.

I claim:

A new and distinct variety of rose plant characterized as to novelty by its vigorous habit of growth, excellence of form of its flowers, the consistent curl of the petals thereof, and the unique coloring of the blooms, substantially as shown and described.

GEORGE OHLHUS.

No references cited.